(12) United States Patent
Naghavi et al.

(10) Patent No.: US 10,631,771 B2
(45) Date of Patent: Apr. 28, 2020

(54) METHODS AND APPARATUS FOR BLOOD SAMPLING

(76) Inventors: Morteza Naghavi, Houston, TX (US); Albert Andrew Yen, Pearland, TX (US); Haider Hassan, Houston, TX (US); David Panthagani, Houston, TX (US); Craig Jamieson, Houston, TX (US); Gary L. McQuilkin, Plymouth, MN (US); Timothy J O'Brien, St. Francis, MN (US)

( * ) Notice: Subject to any disclaimer, the term of this patent is extended or adjusted under 35 U.S.C. 154(b) by 350 days.

(21) Appl. No.: 12/349,068

(22) Filed: Jan. 6, 2009

(65) Prior Publication Data
US 2009/0177224 A1    Jul. 9, 2009

Related U.S. Application Data (60) Provisional application No. 61/019,470, filed on Jan. 7, 2008.

(51) Int. Cl.
*A61B 5/15* (2006.01)
*A61B 5/157* (2006.01)

(52) U.S. Cl.
CPC .................................. *A61B 5/157* (2013.01)

(58) Field of Classification Search
CPC . A61B 17/132; A61B 17/135; A61B 17/1355; A61B 5/150053–5/150068; A61B 5/150106–5/150114; A61B 5/157
USPC ............. 600/579, 583; 73/748; 606/201–203
See application file for complete search history.

(56) References Cited

U.S. PATENT DOCUMENTS

| | | | | |
|---|---|---|---|---|
| 2,604,098 | A * | 7/1952 | Casimir | 606/203 |
| 4,200,058 | A * | 4/1980 | Happel | 119/14.01 |
| 4,664,651 | A * | 5/1987 | Weinshenker et al. | 604/115 |
| 4,883,462 | A * | 11/1989 | Williamson et al. | 604/540 |
| 5,163,442 | A * | 11/1992 | Ono | 600/573 |
| 5,518,006 | A * | 5/1996 | Mawhirt | A61B 5/15142 600/583 |
| 5,540,714 | A * | 7/1996 | Payne et al. | 606/201 |
| 5,607,448 | A * | 3/1997 | Stahl et al. | 606/203 |
| 5,752,512 | A * | 5/1998 | Gozani | A61B 5/05 600/347 |
| 5,893,870 | A * | 4/1999 | Talen | A61B 17/1322 606/201 |
| 5,971,941 | A * | 10/1999 | Simons | A61B 5/14532 600/573 |
| 6,546,893 | B1 * | 4/2003 | Happel et al. | 119/14.47 |
| 6,679,852 | B1 * | 1/2004 | Schmelzeisen-Redeker et al. | 600/583 |
| 2006/0047221 | A1 * | 3/2006 | Gu | A61B 5/411 600/583 |
| 2006/0217636 | A1 * | 9/2006 | Braig | A61B 5/14514 600/583 |
| 2009/0198152 | A1 * | 8/2009 | Kim | 600/583 |
| 2009/0270910 | A1 * | 10/2009 | Hargens et al. | 606/201 |

\* cited by examiner

*Primary Examiner* — Devin B Henson
*Assistant Examiner* — H. Q. Nguyen
(74) *Attorney, Agent, or Firm* — Frank Pham; Pham IP Group (57) ABSTRACT

Methods and apparatus for blood sampling from skin capillaries are provided. Blood extraction is improved by applying gradient pressure in a proximal to distal direction of an extremity. Blood is extracted and sampled from the skin capillaries with a blood sampling mechanism of at least a lancet and testing kit.

4 Claims, 7 Drawing Sheets

METHODS AND APPARATUS FOR BLOOD SAMPLING

CROSS REFERENCE TO RELATED APPLICATIONS

This application claims priority based on U.S. Provisional Application No. 61/019,470, filed Jan. 7, 2008, the disclosure of which is incorporated herein by reference in its entirety.

FIELD OF THE INVENTION

This invention relates to methods and apparatus for blood sampling. More particularly, this invention relates to enhancing blood sampling to improve speed, repeatability, comfort, and safety of blood testing.

BACKGROUND OF THE INVENTION

Without limiting the scope of the invention, its background is described in connection with sampling of blood. Particularly popular for glucose measure measurements, blood sampling devices, also known as lancing devices, are known for piercing the skin to produce blood for analysis. Typically, a drop of blood for this type of analysis is obtained by making a small incision in the skin with a quick-action fine needle, or lancet, to create a small wound that generates a small blood droplet on the surface of the skin. However, repeatability, comfort, and safety of lancing devices have been limited up to this point.

For example, early methods of lancing included piercing or slicing the skin with a needle or razor. Current methods utilize lancing devices that drive the lancet by a variety of mechanisms such as springs, pistons, and lasers. The tests are performed by a prick of a finger with a lancet to get a drop of blood. For example, the device may be held against the skin and mechanically triggered to launch the lancet as a retractable projectile. Unfortunately, the pain associated with a lancing event using known technology often discourages patients from testing and subsequent compliance. Further, in addition to vibratory stimulation of the skin as the lancet impacts the end of a launcher stop, known spring based devices can also cause recoil and multiple strikes because of the possibility of harmonically oscillating against the patient tissue.

Another barrier to patient compliance is the lack of spontaneous blood flow generated by known lancing technology. In addition to the pain as discussed above, a patient may need more than one lancing event to obtain a blood sample since spontaneous blood generation is unreliable using known lancing technology. Thus the pain is multiplied by the number of tries it takes to successfully generate spontaneous blood flow. Different skin thickness and amounts of vasoconstriction may yield different results in terms of pain perception, blood yield and success rate of obtaining blood between different users of the lancing device.

A still further barrier to improved compliance is the many steps and hassle associated with each lancing event. Many patients need to self-test for blood component levels five to six times daily. The large number of steps required in traditional methods of blood testing, ranging from lancing, to milking of blood, applying blood to the test strip, and getting the measurements from the test strip, discourages many patients from testing their blood as often as recommended. Older patients and those with deteriorating motor skills encounter difficulty loading lancets into launcher devices, transferring blood onto a test strip, or inserting thin test strips into slots on blood measurement meters. Additionally, the wound channel left on the patient by known systems may also be of a size that discourages those who are active with their hands or who are worried about healing of those wound channels.

Accordingly, what are needed are methods and apparatus to deliver improved speed, repeatability, comfort, and safety to lancing devices for blood sampling.

BRIEF SUMMARY OF THE INVENTION

Provided herein are methods and apparatus for blood sampling from skin capillaries. In one embodiment, blood extraction is improved by applying gradient pressure in a proximal to distal direction of an extremity. In one embodiment, blood is extracted and sampled from the skin capillaries with a blood sampling mechanism of at least a lancet and testing kit.

In an embodiment, improved blood extraction is provided in a distal region of an individual (e.g. an arm, leg, or any digit such as a finger or toe) by applying gradient pressure in a proximal to distal direction in the individual, inducing reactive hyperemia, or combinations thereof. In an embodiment, improved blood extraction in a distal region of an individual can be provided by apparatus including but not limited to a plurality of cuffs, an advancing tourniquet, a single cuff pressed against a hard surface, a rolling ring, or combinations thereof. In an embodiment, blood pooling can be maintained in the distal region of the individual by applying pressure at a level adjusted to only occlude venous flow.

In an embodiment, blood sampling of distal regions of an individual can be provided by a lancet and testing kit. In an embodiment, the blood sampling of distal regions of an individual can feature additional components including but not limited to bandaging, cooling, absorption, cleaning, and anti-coagulating applications. The apparatus may be manual or automated. In one embodiment the apparatus includes a programmable monitor for instructing blood sampling in accordance with a schedule.

BRIEF DESCRIPTION OF THE DRAWINGS

FIGS. 3A-3C depict embodiments of several components of a blood sampling mechanism.

BRIEF DESCRIPTION OF THE INVENTION

Disclosed herein are novel methods and apparatus for improving speed, repeatability, comfort, and safety of blood sampling. In one embodiment, these improvements are provided by extraction of blood from skin capillaries upon applying gradient pressure in a proximal to distal direction of an extremity. In one embodiment, blood is extracted and sampled from the skin capillaries with a blood sampling mechanism of at least a lancet and testing kit. The invention relies, at least in part, on physiologic reactions in the tissue of blood extraction to reactive hyperemia and/or applications of pressure in a distal direction.

As used herein the term "blood sampling" means pricking the skin, extracting and collecting a fluid sample from the site of the skin prick, and testing the fluid sample. By "distal extremity" it is meant the hands and feet, including the digits of the hands and feet. By "proximal" and "distal" it is meant relative references to anatomical location, where "proximal" refers to a location in the body that is situated nearer to point of attachment or origin and "distal" refers to a location in the body that is situated farther from point of attachment or origin. By "regional" or "local" it is meant administration to a defined area of the body as contrasted with systemic administration. By "blood" it is meant a specialized bodily fluid (technically a tissue) that is composed of a liquid called blood plasma and blood cells suspended within the plasma. However, references to "blood" as described herein can also refer to any other suitable bodily fluids that can be sampled, such as plasma for example. "Vasodilation" refers to the widening of blood vessels resulting from relaxation of the muscular wall of the vessels.

Improving Blood Extraction by Applying Gradient Pressure and/or Inducing Reactive Hyperemia One embodiment of the present invention employs automated application of pressure in a proximal to distal direction in an individual to replicate squeezing or milking motions for blood extraction. When lancing, a patient strives for a sample big enough for an accurate measurement yet small enough to minimize pain and bruising. Most require a milking motion of the lanced finger to squeeze enough blood out for extraction. By "milking the finger," it is meant stroking and pulling outward in a distal direction, from the base of the finger toward the tip and the sample site. In an embodiment, the present invention aims to automate the process in an efficient, comfortable, and safe manner.

Further, one embodiment of the present invention employs controlled administrations of ischemia to improve vasodilation of distal tissues for blood extraction. One physiologic reaction to local ischemia in normal individuals is reactive hyperemia to the previously ischemic tissue. "Reactive hyperemia" is a term that can be defined as an increase in blood flow to an area that occurs following a brief period of ischemia (e.g., arterial occlusion). Arterial occlusion results in lack of oxygen (hypoxia) as well as an increase in vasoactive metabolites (including adenosine and prostaglandins) in the tissues downstream from the occlusion. Reduction in oxygen tension in the vascular smooth muscle cells surrounding the arterioles causes relaxation and dilation of the arterioles and thereby decreases vascular resistance. When the occlusion is released, blood flow is normally elevated as a consequence of the reduced vascular resistance.

Automated Blood Sampling with a Plurality of Cuffs

Figure 1:
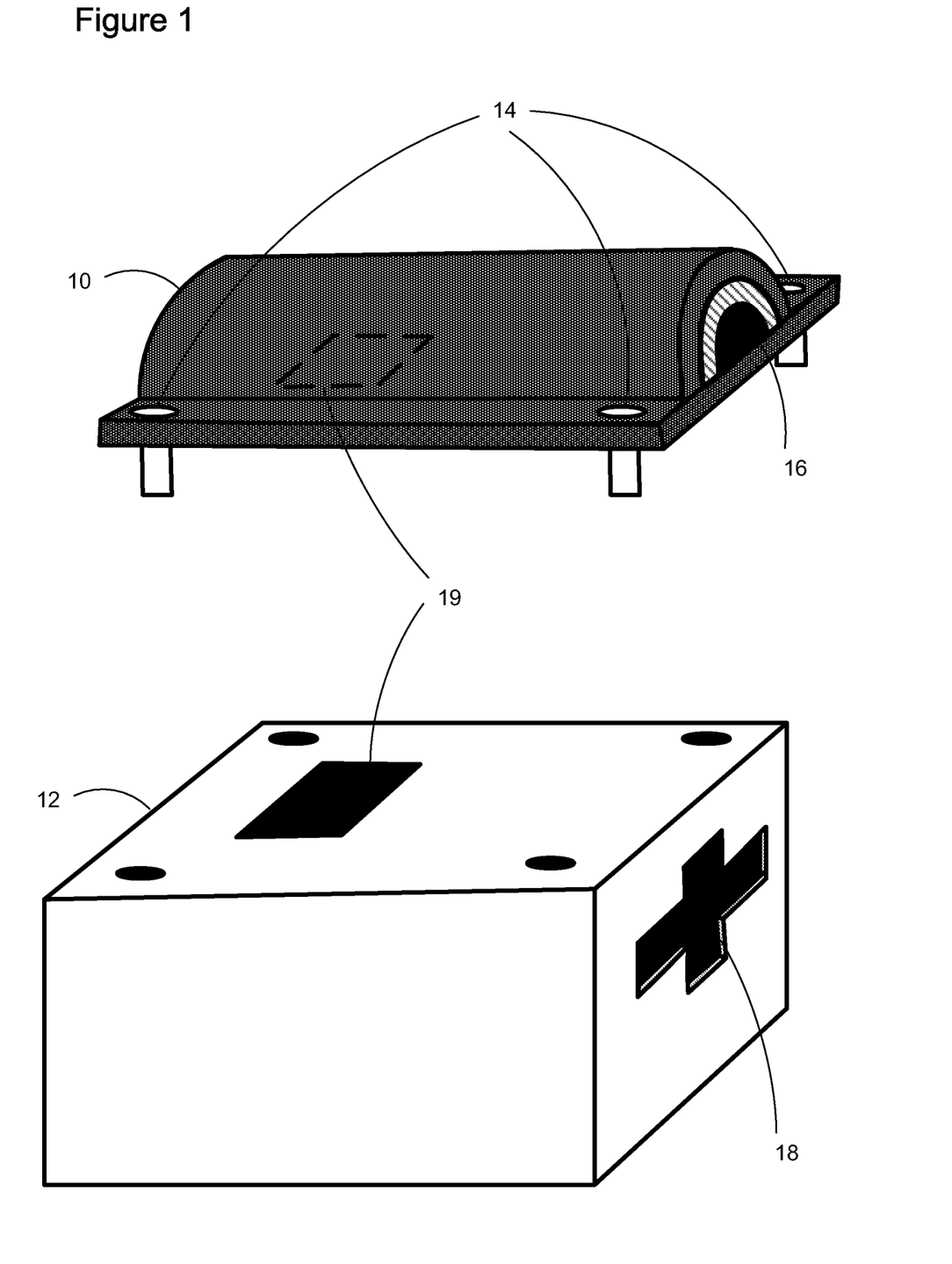
FIG. 1 depicts an embodiment of a system for automated blood extraction, collection, and analysis from the finger using a plurality of cuffs.

In an embodiment, a device for automated blood extraction, collection, and sampling can be provided using a plurality of cuffs to induce reactive hyperemia and/or apply pressure in a distal direction for blood extraction. For example, FIG. 1 depicts an embodiment of a system for automated blood extraction, collection, and analysis from the finger using a plurality of cuffs. The system can be comprised of two main components: a finger enclosure (10) and a blood sampling mechanism (12). In an embodiment, the entire system can be enclosed by any suitable securing mechanism, such as the depicted fasteners (14) and holes, so that, from the outside, the only parts that are visible are a finger shaped opening (16) and one or more slots (18) for a test tray. In an embodiment, openings (19) in the finger enclosure and blood sampling mechanism can be lined up once the entire system is enclosed to provide interactions between the finger and blood sampling mechanism.

Considering the finger enclosure in more detail, the finger enclosure can house the finger of a subject throughout the blood extraction. Any enclosure suitable for the invention as described herein can be used. Once the test subject places their finger into the test device, one or more of a plurality of cuffs inside the finger enclosure can inflate to cause occlusion of one or more arteries and a reactive hyperemia response can result upon release. Alternatively, the cuffs can sequentially inflate, starting at the proximal portion of the finger and continuing to the distal tip of the finger. For example, a second distal cuff can inflate once a first proximal cuff has completely inflated, and a third more distal cuff can inflate once the second cuff has completely inflated, and so on. Accordingly, similar to the squeezing or milking method, blood can be pushed toward the distal tip of the finger where the extraction site is located. Once a final cuff is inflated, there can be a temporary build-up of blood in the distal pulp of the finger and a lancet from the blood sampling mechanism can be pressed against the pulp of the finger through an opening in the finger enclosure.

Figure 2A:
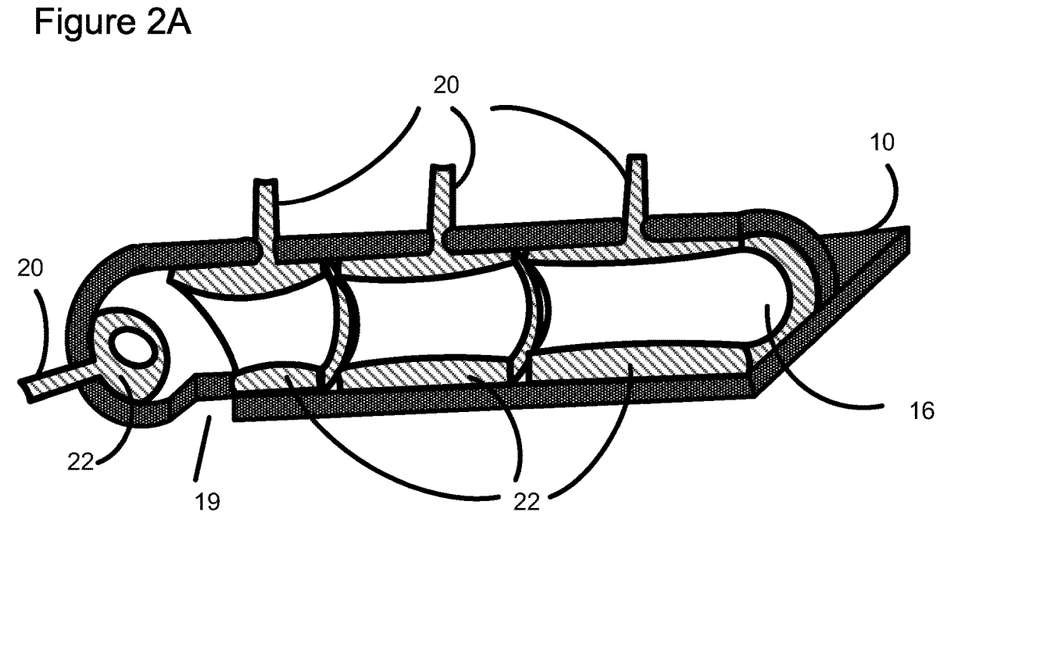
FIG. 2A depicts a cross section view of an embodiment of a finger enclosure housing a plurality of cuffs.
Figure 2B:
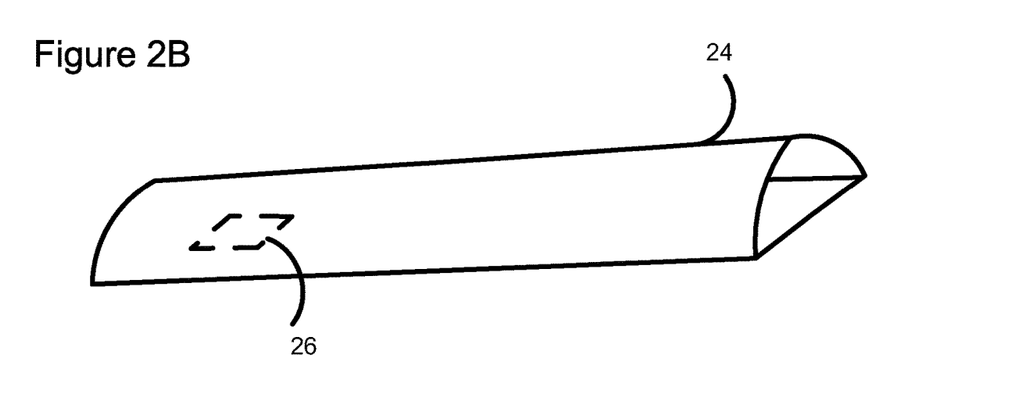
FIG. 2B depicts a finger cover that may be used with the enclosure of FIG. 2A.

FIG. 2A depicts a cross section view of an embodiment of a finger enclosure housing a plurality of cuffs. As depicted, it can provide the enclosure (10) with the opening (16) for the finger and the hole (19) to allow the various components of the blood sampling mechanism to have access to the finger. There are four air inlets (20) that penetrate the wall of the cylinder and empty into four separate inflatable cuffs (22) that line the inner wall. Three of the cuffs are cylindrical in shape, while the cuff that is on the capped wall of the cylinder is shaped like a hemispherical shell. Air tubes can be attached to the air inlets in order to connect the cuff housing to an air pump. This entire assembly consisting of the enclosure, inflatable cuffs, air tubes and air pump can be a removable part of the device. Further, in order to maintain sterility, the test subject can choose to wear a finger cover (24), such as that depicted in FIG. 2B, that is specifically designed to fit into the enclosure and form a barrier between the cuffs and the skin of the subject. In an embodiment, the finger cover (24) can have an opening (26) to line up with the hole (19) in the finger enclosure.

Considering the blood sampling mechanism in more detail, the blood sampling mechanism can allow for several interactions with the finger through the opening in the finger enclosure. For example, as the lancet deploys, it can be immediately retracted into the sampling mechanism and moved away from the finger tip, allowing a small amount of blood to collect on the surface of the skin. Further, a test strip with one or more attached capillary tubes can be moved toward the tip of the finger. As the strip moves toward the opening in the finger enclosure, the capillary tubes can contact with the subject's blood. Accordingly, by capillary action, blood can be transferred from the tip of the finger to the test strip. After enough blood has been collected on the test strip, the finger cuffs can simultaneously deflate and the test strip can be retracted into the sampling mechanism. Similarly, other components such as a bandage can be moved over the opening in the finger enclosure by the sampling mechanism. In an embodiment, the same mechanism that pushes the lancet into the finger of the subject finger can push the additional components to the finger. After all the desired components have been applied, the subject can be instructed to remove their finger from the enclosure and the results of the test can be displayed and/or printed.

Figure 3A:
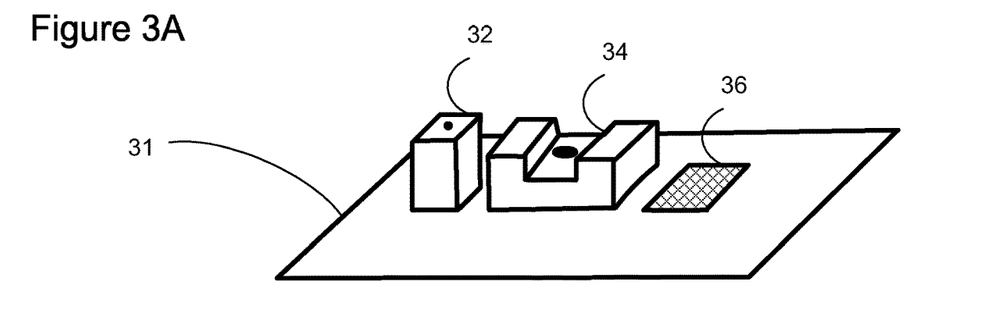
FIG. 3A depicts an embodiment of a test tray for a blood sampling mechanism.
Figure 3B:
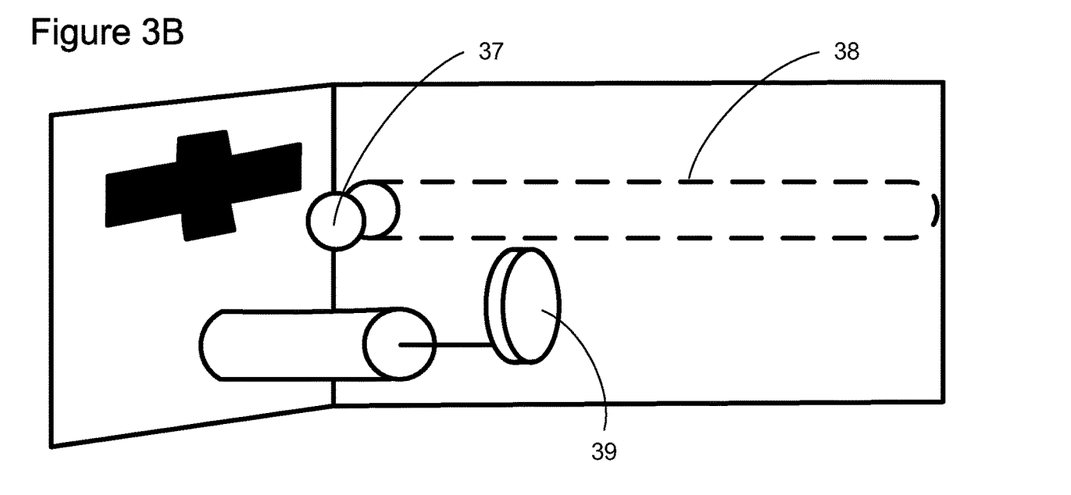
FIG. 3B depicts an embodiment of a conveyor system and cam system for a blood sampling mechanism.
Figure 3C:
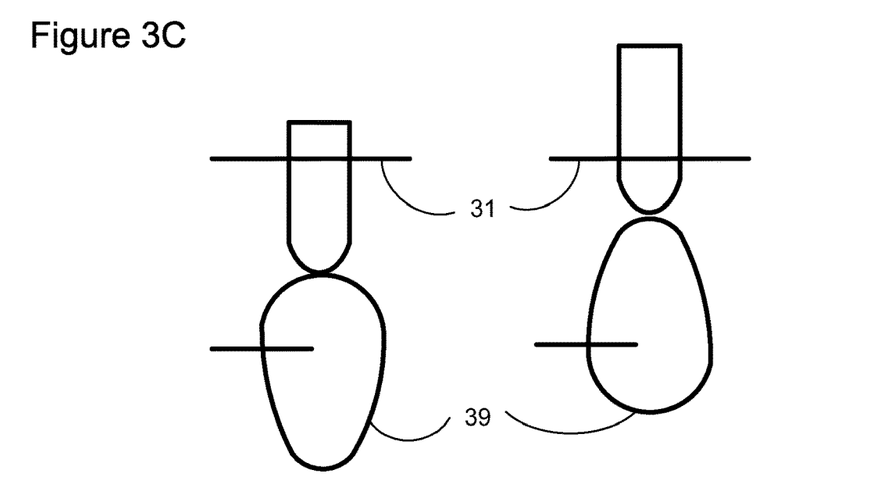
FIG. 3C depicts an embodiment of a cam system for a blood sampling mechanism.

FIGS. 3A-3C depict embodiments of several components of a blood sampling mechanism. FIG. 3A depicts an embodiment of a test tray for a blood sampling mechanism. In an embodiment, a disposable lancet (32), test strip (34), and bandage (36) can be provided in a test tray (31) as depicted. In an embodiment, all or portions of the test tray can be disposable. The lancet can be a single or multiple use device that deploys and quickly retracts when the lancet enclosure portion of the test tray is pressed against the skin. The lancet, test strip, and bandage can be mounted to the tray so that they are able to move independently of the tray. The lancet, test strip, and bandage can be mounted sequentially as depicted or in any arrangement suitable for the methods as described herein. The tray can be inserted into the blood sampling mechanism and can be advanced into the enclosure by a conveyor system. The tray can exit the back of the device where the test strip from the tray can be removed and placed it into a reader or printer to get results.

FIG. 3B depicts an embodiment of a conveyor system and cam system for a blood sampling mechanism. The conveyor system can include a motor (37) and belt (38), both of which are attached to an interior side of a wall within the blood sampling mechanism, that can move and stop the tray when the lancet, test strip, bandage, and any other components that are located directly under the finger tip opening. Once a component has been deployed, the conveyor system can advance the tray until a next component is under the finger opening. For example, once the lancet is deployed, the conveyor system can advance the tray until a test strip is under the finger opening for deployment. In an embodiment, the conveyor can be manually operated. In an embodiment, the conveyor can be semi or fully automated. In an embodiment, the conveyor system can be located anywhere within a blood sampling enclosure. In an embodiment, a cam (39) can be used to move the conveyor system of the blood sampling mechanism. In an embodiment, a cam (39) can be located independent of the conveyor system. In an embodiment, a cam (39) can be aligned with a test tray.

FIG. 3C depicts an embodiment of a cam system for a blood sampling mechanism. In an embodiment, the cam system can rotate an automated cam (39) to deploy a lancet, test strip, bandage, and/or any other components of a test tray (31). For example, once the lancet is located directly under the finger of a subject and the cuffs in the finger enclosure have inflated creating a temporary buildup of blood in the finger tip, the cam can be quickly rotated so that it presses the lancet against the finger tip until the lancet deploys. The cam can continue to rotate until the lancet is brought back into its lowest position. At this time the conveyor can advance the tray until the next component, e.g. a test strip, is under the finger tip. In a similar manner, the cam can deploy the test strip toward the finger of the subject. In an embodiment, operation of the conveyor system and cam system can be adjusted to allow for appropriate timing necessary for each component. For example, after lancing, the tray can be held at the finger opening for a predetermined amount of time to deploy a test strip by the cam and thus allow blood to collect on the strip. The cam can then rotate and lower the test strip to its lowest position and can be advanced by the conveyor system. Once the cam lowers the final component, e.g. a bandage, the tray can advance through a test tray opening in the device.

Manual Blood Sampling Device

Figure 4A:
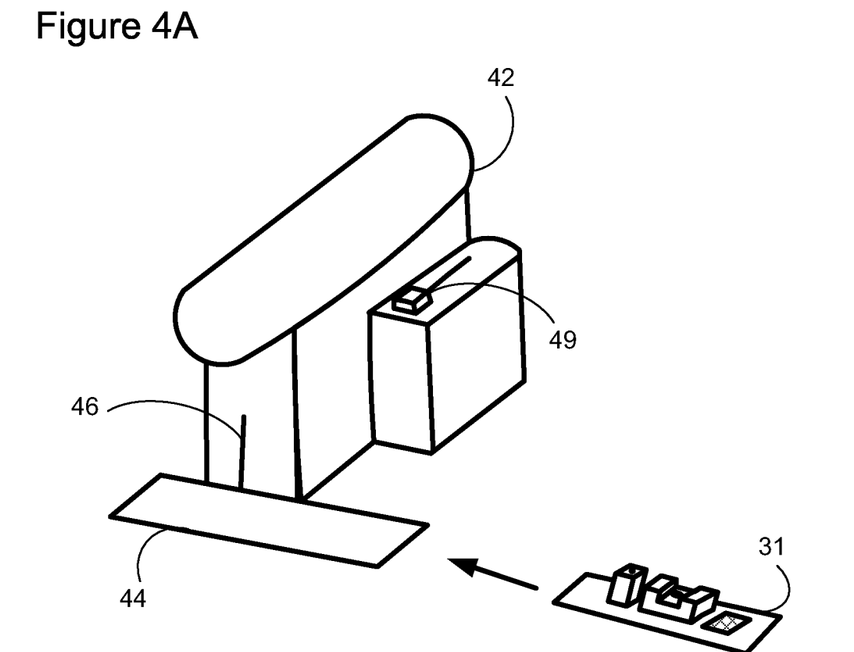
FIGS. 4A and 4B depict several views of an embodiment of a system for manual blood extraction, collection, and analysis from the finger using a plurality of cuffs.
Figure 4B:
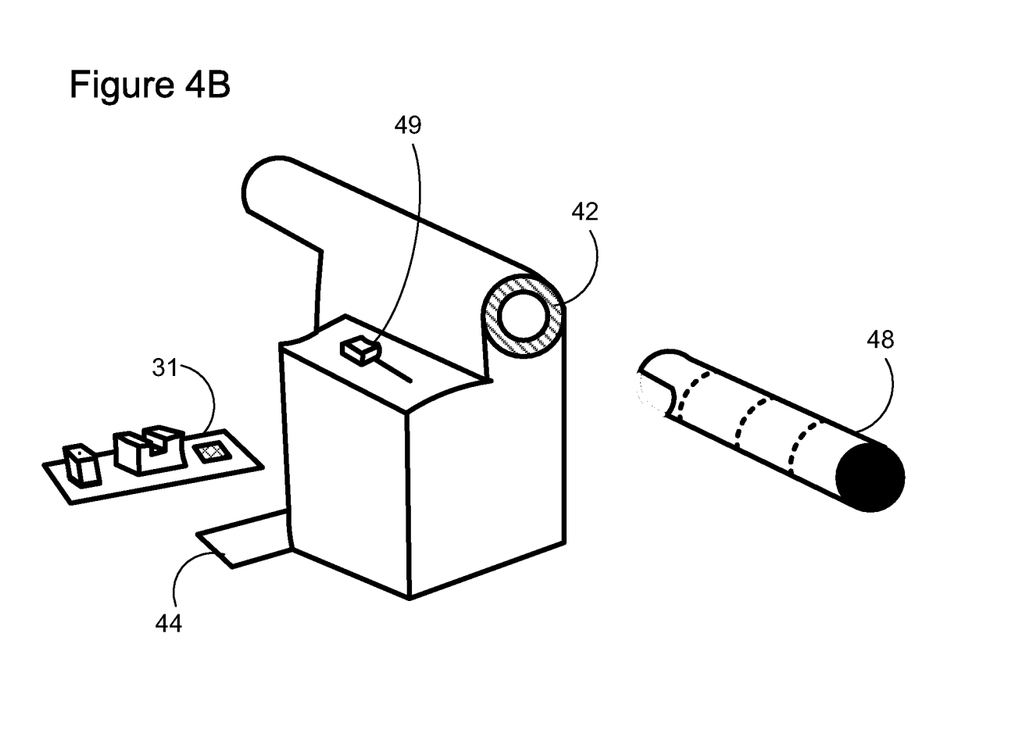

In an embodiment, a device for manual blood extraction, collection, and sampling can be provided to induce reactive hyperemia and/or apply pressure in a distal direction for blood extraction. For example, FIGS. 4A and B depict several views of an embodiment of a system for manual blood extraction, collection, and analysis from the finger. The system can be comprised of a finger occluding mechanism (42), a test tray (31), a tray slide (44), a vertical slide (46), and a finger cover (48). The occluding mechanism can allow for a subject to insert their finger into the device for occlusion of the finger using any suitable means, e.g. an inflatable cuff or an adjustable tourniquet controlled by a slide controller (49) as depicted. The occluding mechanism can accordingly cause a temporary buildup of blood in the pulp of the finger. The subject can also use their other free hand to manually advance a test tray along a tray slide. Once the tray is positioned so that a desired component is directly under the fingertip, the component can be manually advanced to and retracted from the fingertip by a vertical slide. For example, the tray can be advanced along the tray slide until the lancet is directly under the finger tip. The entire tray can then be moved toward the finger tip until the lancet has deployed. The tray can then be moved back down the vertical slide and advanced along the tray slide so that a test strip rests under the finger. Similarly, the test strip and subsequent components of the tray can be advanced to the finger and retracted by the same mechanism until all desired components have been deployed. All or portions of the test tray can be either disposable or reusable. In an embodiment, the occluding mechanism can include a finger cover that can be reusable or disposable to improve sterility and hygiene of the system which is especially important for multiple uses.

Considering the finger occlusion mechanism in more detail, the openings on this device can be the finger opening where the subject inserts their finger and a testing opening where the interactions with the test tray can occur. In an embodiment, the finger can remain in the occlusion mechanism throughout the blood extraction process. In an embodiment, the subject can use a thumb of the testing hand or the available free hand to move a slide controller until the finger is adequately occluded. In an embodiment, the slide controller can tighten any suitable occlusion mechanism around the finger, including but not limited to a tourniquet, one or more inflatable cuffs, and/or an adjustable plastic band. In an embodiment, the finger enclosure can be designed so that the top of the finger is completely covered. In an embodiment, the part of the finger that is accessible by the test tray is limited to the lower pulp of the fingertip. In an embodiment, the top of the finger can be covered so that it cannot be moved away from the lancet, test strip, and/or any components on the test tray.

Considering the test tray in more detail, the tray can contain any suitable configuration of one or more necessary components, such as a lancet, test strip and bandage. In an embodiment, the test tray can fit and be placed on a tray slide that is designed to move up and down when one of the components on the tray is located directly under the finger. In an embodiment, the tray can attach to the slides so that it cannot be accidentally removed during the blood extraction and sampling. The slide and tray can move as one when the tray is attached to the finger occlusion device. Once the blood extraction has been completed, the entire tray can be removed from the slide. In an embodiment, some components such as a test strip can be removed from the tray for further analysis or reuse. In an embodiment, all or portions of the tray can be discarded after use.

Advancing Tourniquet Occlusion Mechanism

Figure 5A:
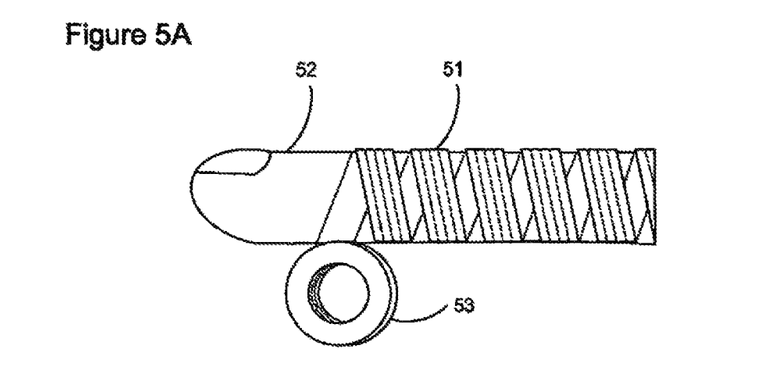
FIGS. 5A and 5B depict embodiments of an advancing tourniquet device for use on a finger.
Figure 5B:
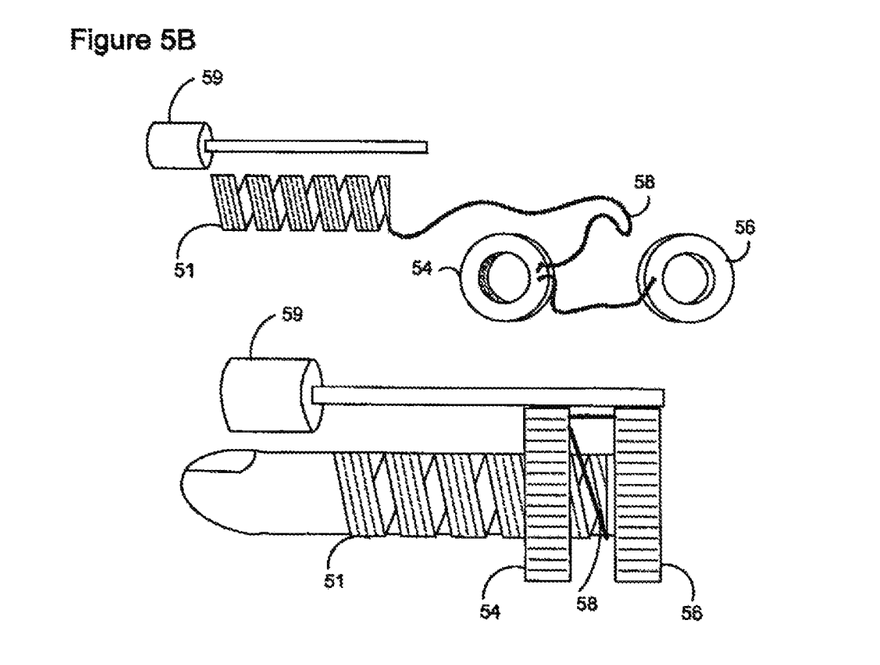

In an embodiment, a device for an advancing tourniquet occlusion mechanism can be provided to induce reactive hyperemia and/or apply pressure in a distal direction for blood extraction. For example, FIGS. 5A and 5B depict embodiments of an advancing tourniquet device for use on a finger. A string or cable can be used as a tourniquet placed around the finger of a subject. The tourniquet can be wrapped from the base of the finger toward the tip of the finger as to create a bolus of blood in the fingertip. As depicted in FIG. 5A, the advancing tourniquet (51) can be applied around a finger (52) by rolling a dispenser, such as the depicted ring (53), around the finger.

Further, FIG. 5B depicts an embodiment of an advancing tourniquet that is automated. The system consists of a tourniquet roller (54) and a tourniquet dispenser (56). In an embodiment, a tourniquet (51) and/or tourniquet roller can be threaded and channeled. In an embodiment, the tourniquet dispenser can be spring loaded. A spring loaded tourniquet dispenser can apply tension to the tourniquet so that it wraps tightly around a finger. Thus, a threaded tourniquet can thread into a threaded tourniquet roller similar to a bolt threading into a nut. As depicted, a string or cable (58) for the tourniquet can be fed from the dispenser, through a channel on the tourniquet roller and attached to the base of the tourniquet. As the tourniquet roller turns the thread towards the tip of the tourniquet, the thread or cable is fed into the channel of the tourniquet. This motion wraps the tourniquet around the finger from the base to the tip. In an embodiment, the tourniquet roller and dispenser can be rotated in unison so that the tourniquet is dispensed correctly and does not become incorrectly wrapped around the outside of the tourniquet. Both the tourniquet and dispenser can be the same size and shape to minimize incorrect wrapping. Both can be rotated in unison by an electric motor (59) as depicted herein, or by any mechanism suitable for the description herein.

Single Cuff Occlusion Mechanism

Figure 6:
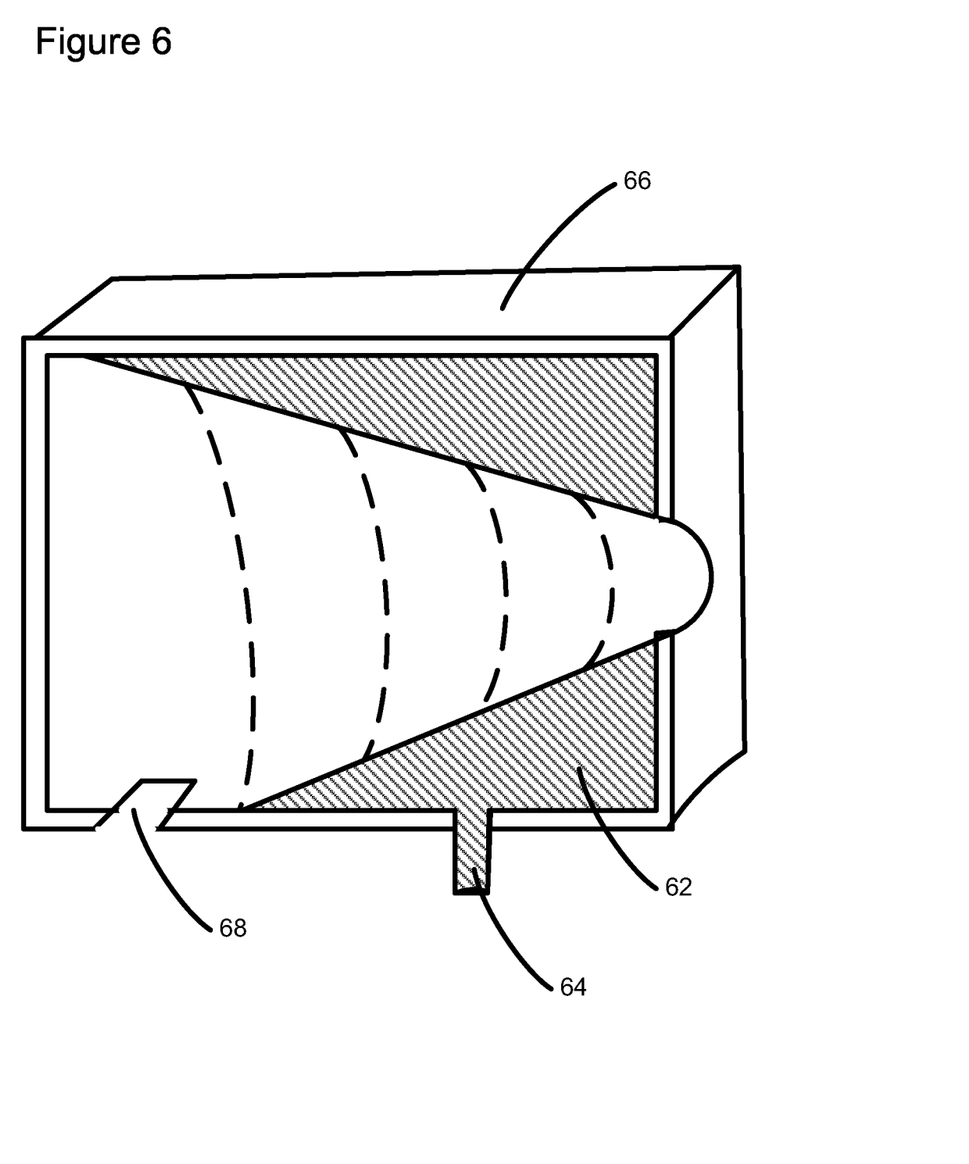
FIG. 6 depicts a cross section view of an embodiment of a single air cuff inside an enclosure for finger blood sampling.

In an embodiment, a device for a single cuff occlusion mechanism can be provided to induce reactive hyperemia and/or apply pressure in a distal direction for blood extraction. For example, FIG. 6 depicts a cross section view of an embodiment of a single air cuff inside an enclosure for finger blood sampling. The air cuff (62) can be positioned in such a way that it is in contact with the base of the finger and slowly tapers away from the finger as it progresses toward the distal tip of the finger. In an embodiment, the cuff can automatically inflate, via one or more air inlets (64), once a finger of the subject is inserted into the device. The cuff can inflate with a uniform pressure in an embodiment. In an embodiment, the inflation of the cuff pressed against the hard surface of an enclosure (66) can exert pressure at the base of the finger and, as more air is forced into the cuff, the cuff can continue to expand toward the distal tip of the finger. Accordingly, blood can be first trapped in the finger by the initial occlusion at the base of the finger and, as the cuff inflates toward the distal tip of the finger, more trapped blood can be pushed toward the tip of the finger as well. In an embodiment, the cuff can be inflated to only occlude the base of the finger without expanding toward the distal tip of the finger. Such a partial inflation can be adapted to induce reactive hyperemia for example. In an embodiment, once the cuff has completely inflated, a lancet can be inserted into a lancet opening (68) in the enclosure and used to prick the finger tip and blood can be collected. In an embodiment, the cuff can automatically deflate and the subject can remove their finger from the device after collection of the blood sample. In an embodiment the subject can cover their finger with a finger cover of any material, such as gauze, suitable to create a barrier between any of the permanent parts of the device and to avoid any cross contamination. Such a finger cover can be used in a point of care device to allow for multiple samples from the same device.

Rolling Ring Occlusion Mechanism

Figure 7A:
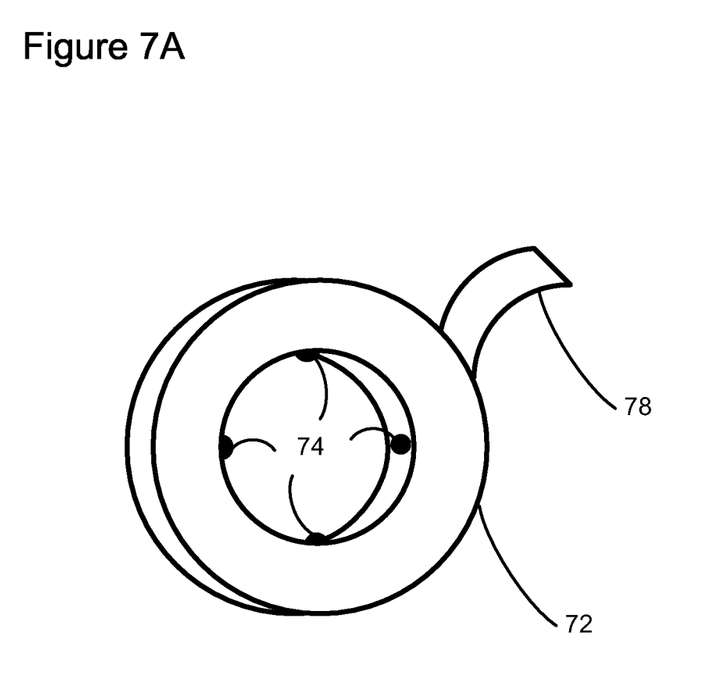
FIGS. 7A and 7B depict an embodiment of a rolling ring occlusion mechanism for finger blood sampling.
Figure 7B:
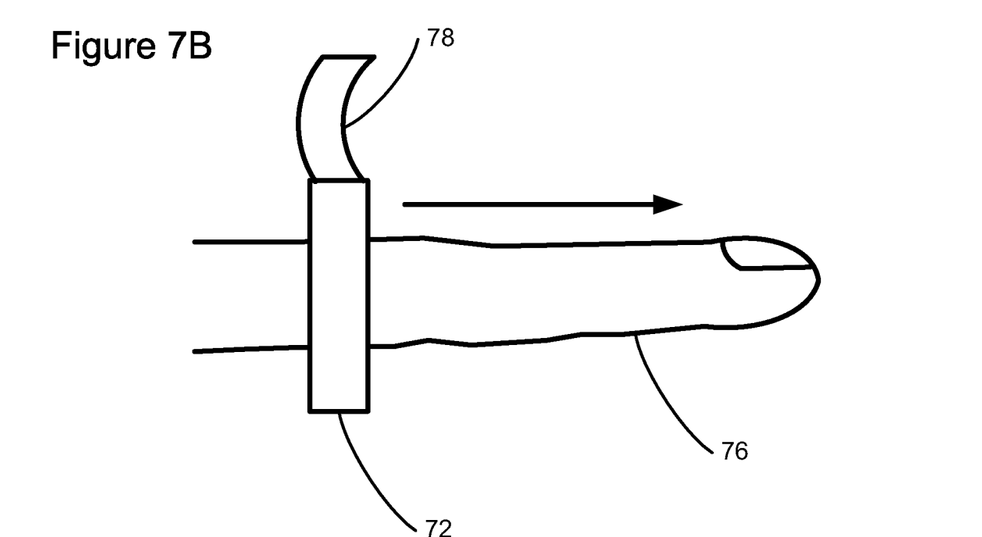

In an embodiment, a device for a rolling ring occlusion mechanism can be provided to induce reactive hyperemia and/or apply pressure in a distal direction for blood extraction. For example, FIGS. 7A and B depict an embodiment of a rolling ring occlusion mechanism for finger blood sampling. As depicted, a ring shaped device (72) can have ballbearings (74) to facilitate proximal to distal movement across a finger (76). Occlusion can be provided upon tightening an adjustable strap (78) that is attached to the ring and controls how tightly the ring fits on the finger. In an embodiment, the ring can have one or more ballbearings to facilitate movement along the desired extremity for blood extraction. In an embodiment, any suitable means to facilitate movement along the desired extremity for blood extraction can be used. Accordingly, blood can be first trapped in the finger by the initial occlusion at the base of the finger upon ring tightening and, as the ring is moved toward the distal tip of the finger, more trapped blood can be pushed toward the tip of the finger as well. In an embodiment, the ring can be tightened to only occlude the base of the finger without being moved toward the distal tip of the finger. Such a tightening can be adapted to induce reactive hyperemia for example. In an embodiment, after the ring has been tightened for occlusion and/or during or after the ring movement along the finger, a lancet can be used to prick the finger tip and blood can be collected. In an embodiment, the ring can loosen by any suitable release mechanism and the subject can remove the ring from their finger after collection of the blood sample.

Blood Pooling

In an embodiment, the level of pressure provided is enough for complete occlusion of arterial and venous blood flow. In an embodiment, pooling of blood at the site of the subject to be sampled can be improved by adjusting levels of pressure to various occlusion levels. For example, the pressure can be adjusted to occlude only venous blood flow exiting the target site while still maintaining the blood flow entering through the arteries. Accordingly, by keeping open the entry and closing the exit of blood flow, pooling can occur at a site to make it more conducive for blood sampling. Levels of pressure to occlude only venous blood flow are well known in the art. For example, a suitable range of pressure to occlude only venous blood flow can be from 0 to 20-50 mm Hg depending on the individual.

Blood Sampling Components

In an embodiment, a lancet and a test strip are the only components needed for blood sampling as described herein. The lancet can be any suitable in the art to perform the skin prick as described herein. The test strip can be any suitable for testing of various fluid analytes, including but not limited to: glucose, total cholesterol, HDL, LDL, triglycerides, blood thrombogenicity or clotting, insulin, hemoglobin A1c, liver enzymes, lipid panels, natriuretic factors, and CRP. Further, in an embodiment, additional components can enhance the blood sampling procedure. For example, a bandaging mechanism can be provided to apply a dressing on the skin prick site after sampling. A cooling mechanism can reduce skin temperature to minimize excessive bleeding. Application of absorptive and/or cleaning materials to the skin prick site can be provided. Anti-coagulants can be provided upon noticing blood that is clotting to minimize repeated pricking.

One or more of the components can be manual or automated in operation. In an embodiment, one or more of the components can be in electrical communication, controlled with, and/or display results via a computer, monitor, printer, and/or any other suitable device. In an embodiment, blood sampling as described herein can be in accordance with a schedule that is automated or manual in operation.

We claim:

1. A self-administered blood sampling apparatus for obtaining a blood sample from a skin prick site, comprising:

a blood sampling enclosure configured for completely enclosing said skin prick site, at least two inflatable cuffs configured to cause controlled ischemia followed by reactive hyperemia and configured to apply gradient pressure from above 0 to 50 mm Hg in a proximal to distal direction causing blood pooling at said skin prick site, and a lancet mechanism configured for puncturing skin at said skin prick site to collect the blood sample.

2. The apparatus of claim 1 further comprises a programmable monitor for automating the said blood sampling apparatus according to a sequence and timed schedule for inflating and deflating the at least two inflatable cuffs, puncturing the skin at said skin prick site, and collecting the blood sample.

3. The apparatus of claim 1, wherein said blood sampling apparatus further comprises an anti-coagulant mechanism.

4. The apparatus of claim 1, wherein said blood sampling apparatus further comprises a cleaning mechanism to clean the skin prick site.

* * * * *